(12) United States Patent
Biedermann et al.

(10) Patent No.: US 11,147,593 B2
(45) Date of Patent: Oct. 19, 2021

(54) BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/006,085

(22) Filed: Aug. 28, 2020

(65) Prior Publication Data

US 2021/0059723 A1  Mar. 4, 2021

Related U.S. Application Data

(60) Provisional application No. 62/893,998, filed on Aug. 30, 2019.

(30) Foreign Application Priority Data

Aug. 30, 2019  (EP) .................................... 19194781

(51) Int. Cl.
*A61B 17/70*  (2006.01)
(52) U.S. Cl.
CPC ...... *A61B 17/7037* (2013.01); *A61B 17/7032* (2013.01)
(58) Field of Classification Search
CPC ............ A61B 17/7032; A61B 17/7037; A61B 17/7038

(Continued)

(56) References Cited

U.S. PATENT DOCUMENTS

| 5,443,467 A | 8/1995 | Biedermann et al. |
| 5,882,350 A | 3/1999 | Ralph et al. |

(Continued)

FOREIGN PATENT DOCUMENTS

| CN | 2803295 Y | 8/2006 |
| CN | 103976785 A | 8/2014 |

(Continued)

OTHER PUBLICATIONS

Extended European Search Report for Application No. 19194781.1, dated Mar. 5, 2020, 8 pages.

(Continued)

*Primary Examiner* — Eduardo C Robert
*Assistant Examiner* — David C Comstock
(74) *Attorney, Agent, or Firm* — Lewis Roca Rothgerber Christie LLP

(57) ABSTRACT

A bone anchoring device includes a receiving part configured to pivotably receive a head of an anchoring element, a pressure member positionable and movable in the receiving part, and an insert member positionable at least partially in the pressure member and movable axially relative to the pressure member between a first position and a second position for exerting an adjustable pressure on the head of the anchoring element. A first engagement structure of the insert member that has at least one of an upwardly facing engagement surface or a downwardly facing engagement surface is configured to engage a second engagement structure of the pressure member to releasably hold the insert member at the first position against movement towards the second position and to releasably hold the insert member at the second position against movement towards the first position.

22 Claims, 17 Drawing Sheets

(58) Field of Classification Search
USPC .................................................. 606/266–270
See application file for complete search history.

(56) References Cited

U.S. PATENT DOCUMENTS

| | | | |
|---|---|---|---|
| 6,248,105 B1 | 6/2001 | Schläpfer et al. | |
| 8,506,609 B2 | 8/2013 | Biedermann et al. | |
| 8,556,938 B2 | 10/2013 | Jackson et al. | |
| 8,888,827 B2 | 11/2014 | Harper et al. | |
| 8,926,671 B2 | 1/2015 | Biedermann et al. | |
| 8,951,294 B2 | 2/2015 | Gennari et al. | |
| 9,155,567 B2 | 10/2015 | Auerbach et al. | |
| 9,603,627 B2 | 3/2017 | Krüger | |
| 9,839,446 B2 | 12/2017 | Biedermann et al. | |
| 9,943,338 B2 | 4/2018 | Biedermann et al. | |
| 10,271,877 B2 | 4/2019 | Biedermann et al. | |
| 10,426,521 B2 | 10/2019 | Mosnier et al. | |
| 2003/0167058 A1* | 9/2003 | Shluzas | A61B 17/7037 606/270 |
| 2005/0154391 A1* | 7/2005 | Doherty | A61B 17/7037 606/278 |
| 2006/0173454 A1 | 8/2006 | Spitler et al. | |
| 2007/0167949 A1 | 7/2007 | Altarac et al. | |
| 2009/0149887 A1 | 6/2009 | Schlaepfer et al. | |
| 2010/0152787 A1 | 6/2010 | Walsh et al. | |
| 2010/0234902 A1 | 9/2010 | Biedermann et al. | |
| 2012/0046701 A1 | 2/2012 | Gennari et al. | |
| 2012/0059426 A1 | 3/2012 | Jackson et al. | |
| 2012/0179209 A1 | 7/2012 | Biedermann et al. | |
| 2013/0096622 A1 | 4/2013 | Biedermann et al. | |
| 2013/0096623 A1 | 4/2013 | Biedermann et al. | |
| 2014/0188173 A1 | 7/2014 | Mishra et al. | |
| 2014/0236239 A1 | 8/2014 | Biedermann et al. | |
| 2014/0257411 A1 | 9/2014 | Rezach | |
| 2014/0277189 A1* | 9/2014 | Spratt | A61B 17/863 606/306 |
| 2015/0080960 A1 | 3/2015 | Biedermann et al. | |
| 2015/0134006 A1 | 5/2015 | Ziolo et al. | |
| 2015/0320465 A1 | 11/2015 | Butler et al. | |
| 2017/0049484 A1* | 2/2017 | Left | A61B 17/7038 |
| 2017/0128104 A1 | 5/2017 | Nichols et al. | |
| 2017/0181776 A1 | 6/2017 | Beretta et al. | |
| 2017/0340360 A1 | 11/2017 | Schlaepfer et al. | |
| 2019/0254716 A1 | 8/2019 | Biedermann et al. | |
| 2019/0298420 A1* | 10/2019 | Mishra | A61B 17/7038 |

FOREIGN PATENT DOCUMENTS

| | | |
|---|---|---|
| CN | 104434283 A | 3/2015 |
| EP | 2 829 243 A1 | 1/2015 |
| EP | 2 851 021 A1 | 3/2015 |

OTHER PUBLICATIONS

European Search Report dated Nov. 17, 2015 for Application No. 15167435.5; (7 Pages).

* cited by examiner

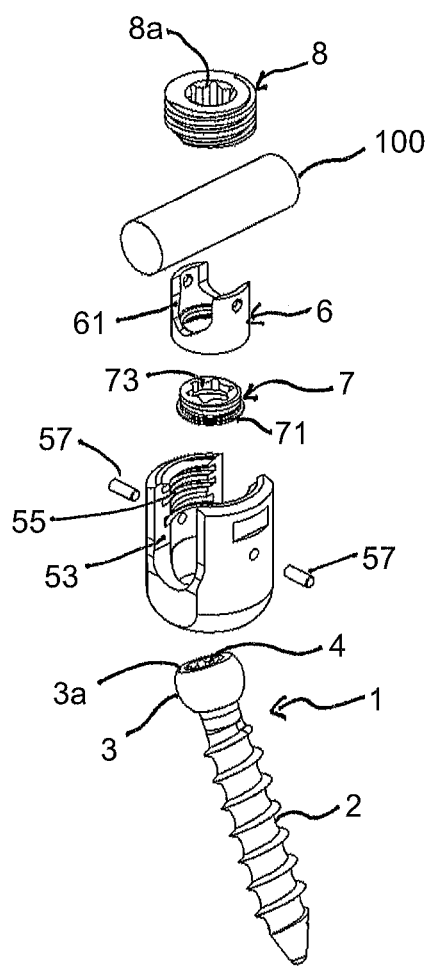
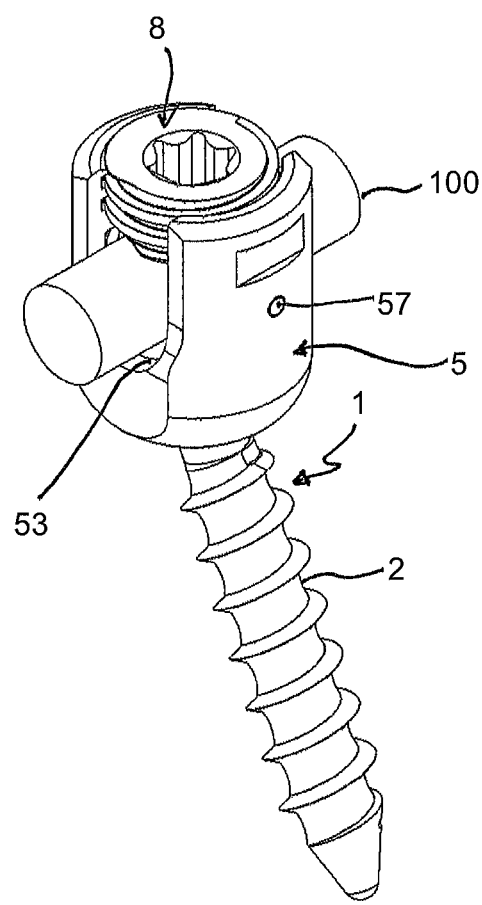
Fig. 1
Fig. 2

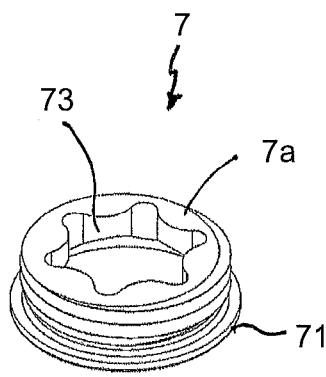
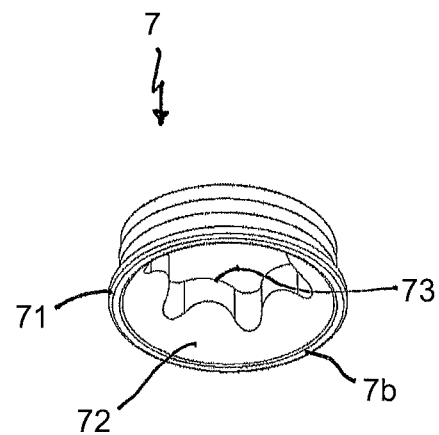
Fig. 12                          Fig. 13
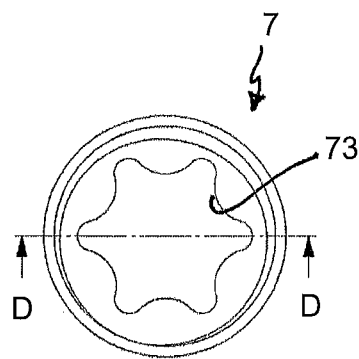
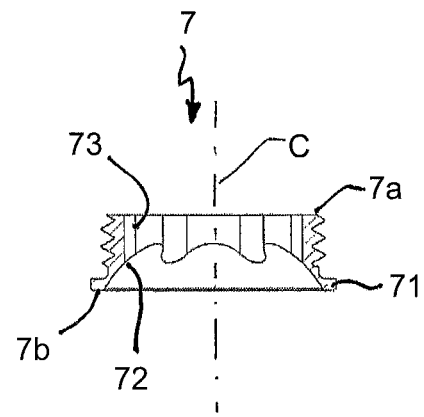
Fig. 14                          Fig. 15
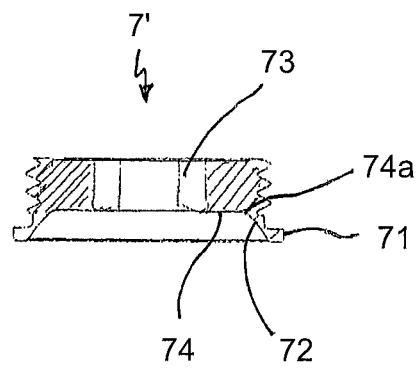
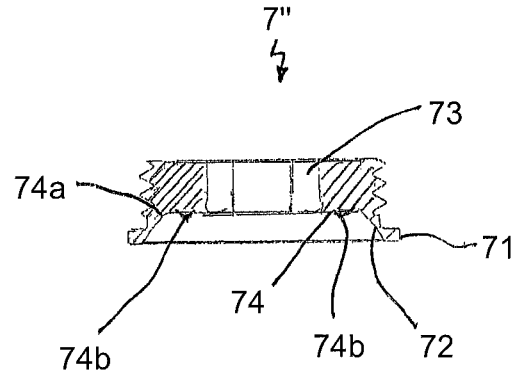
Fig. 16a                         Fig. 16b

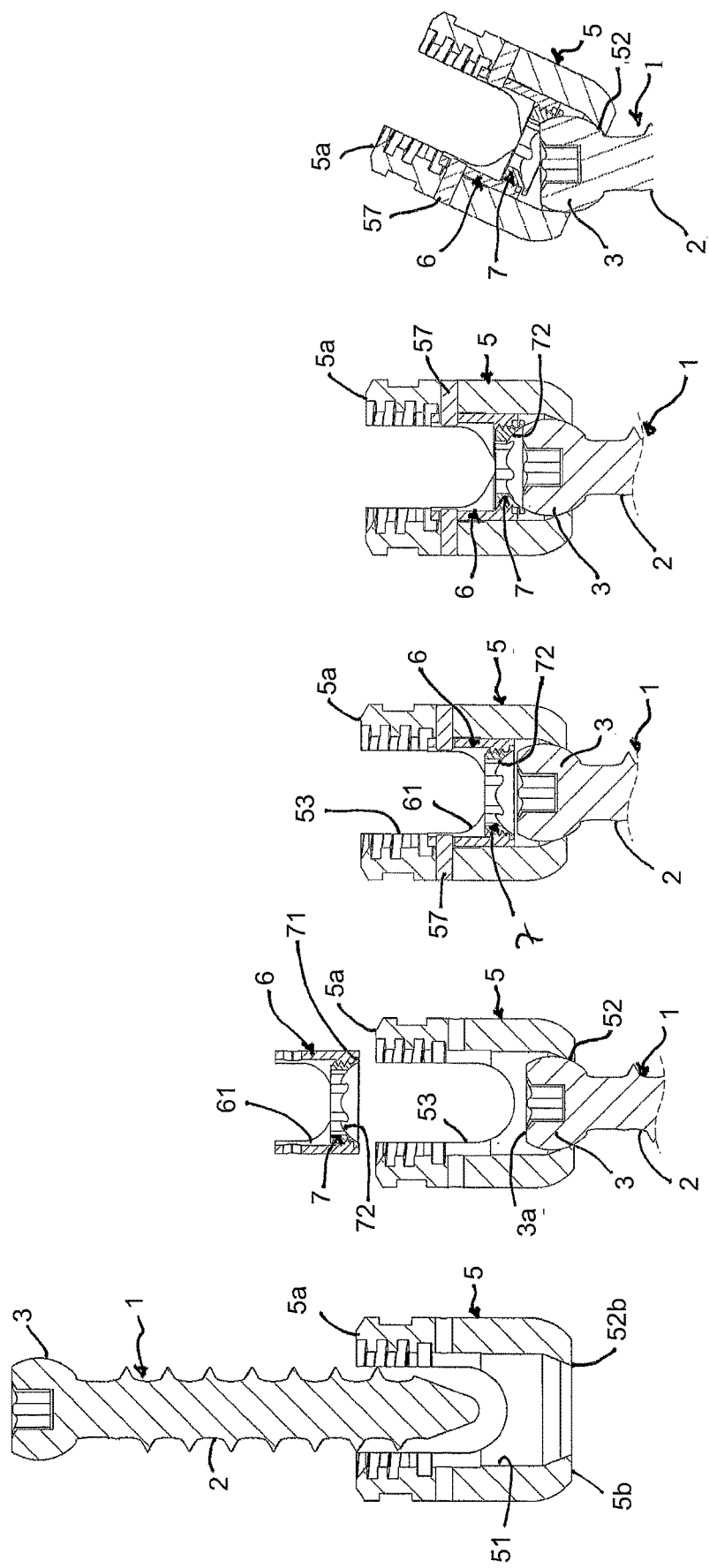

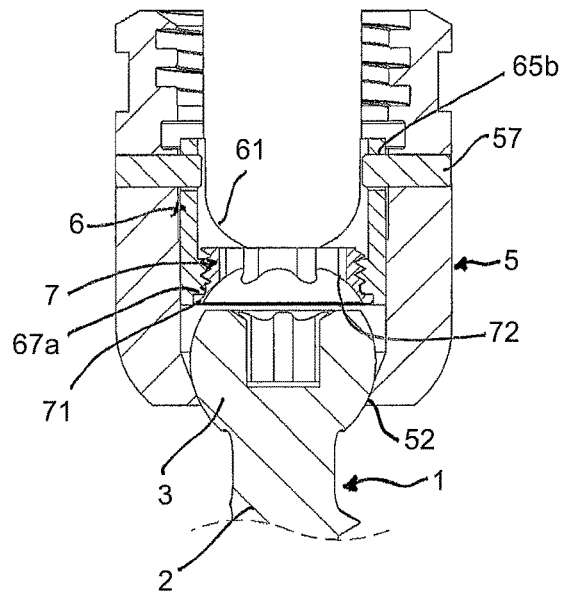
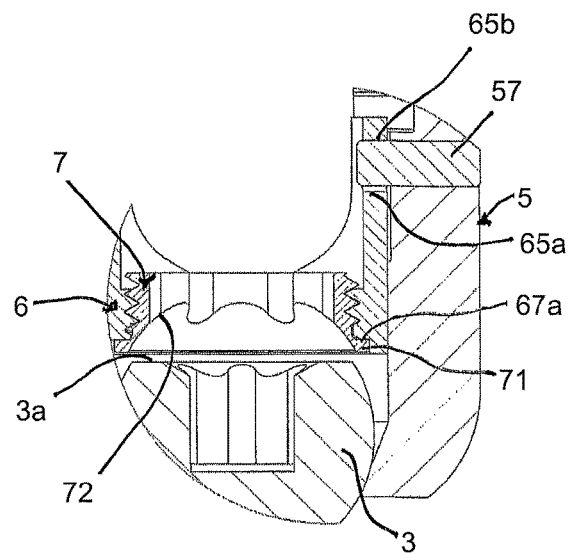
Fig. 18a  Fig. 18b
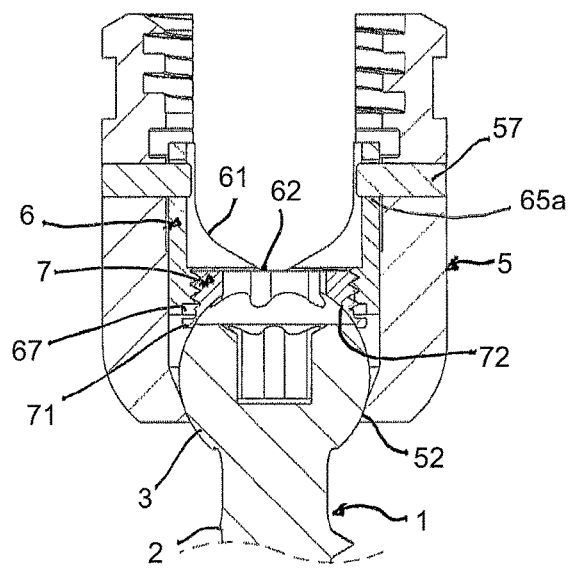
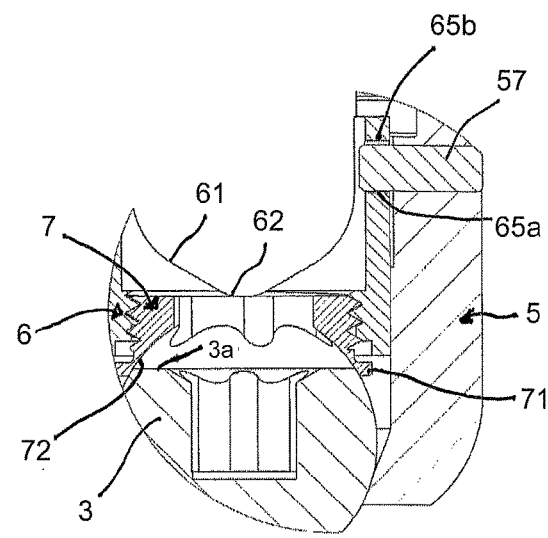
Fig. 19a  Fig. 19b

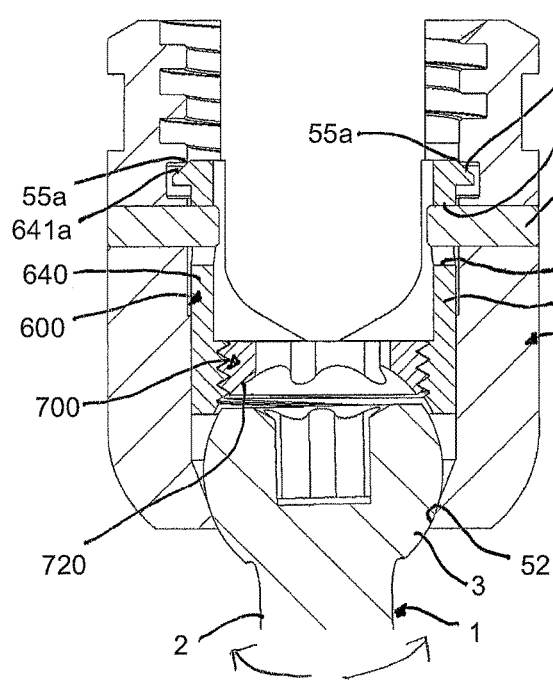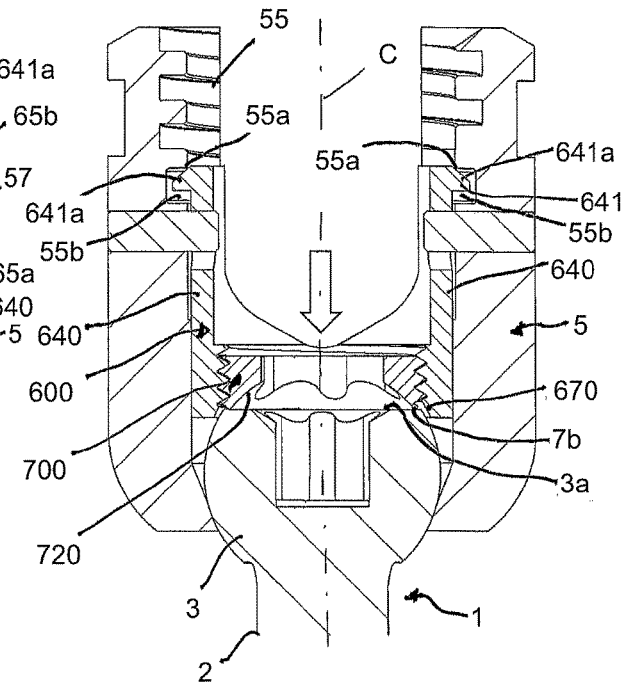
Fig. 28a          Fig. 28b
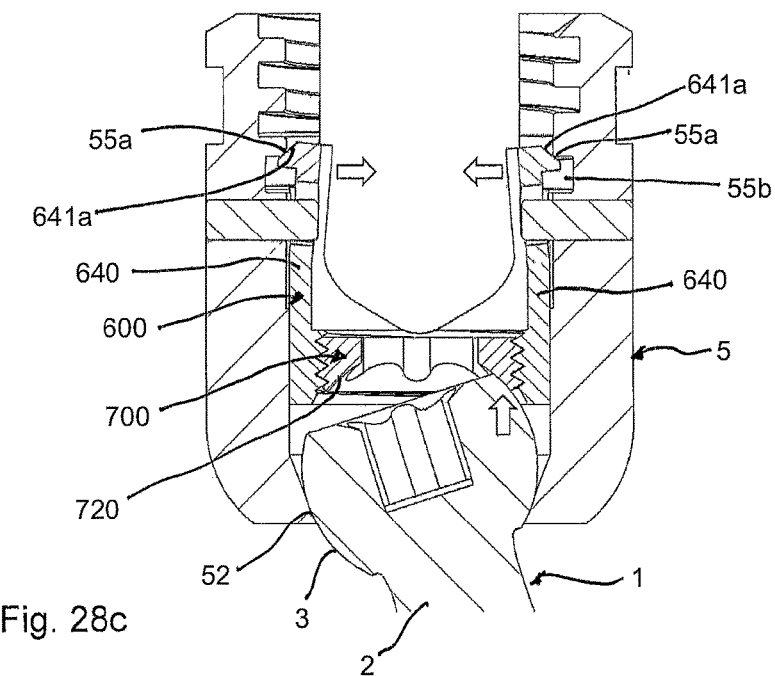
Fig. 28c

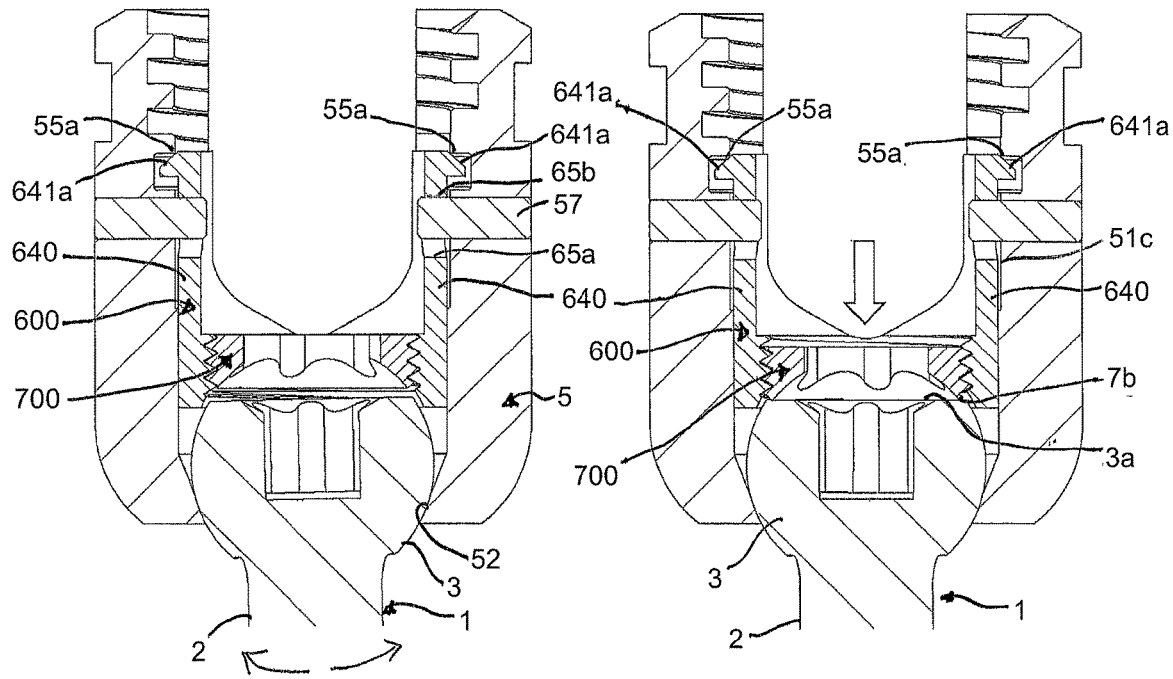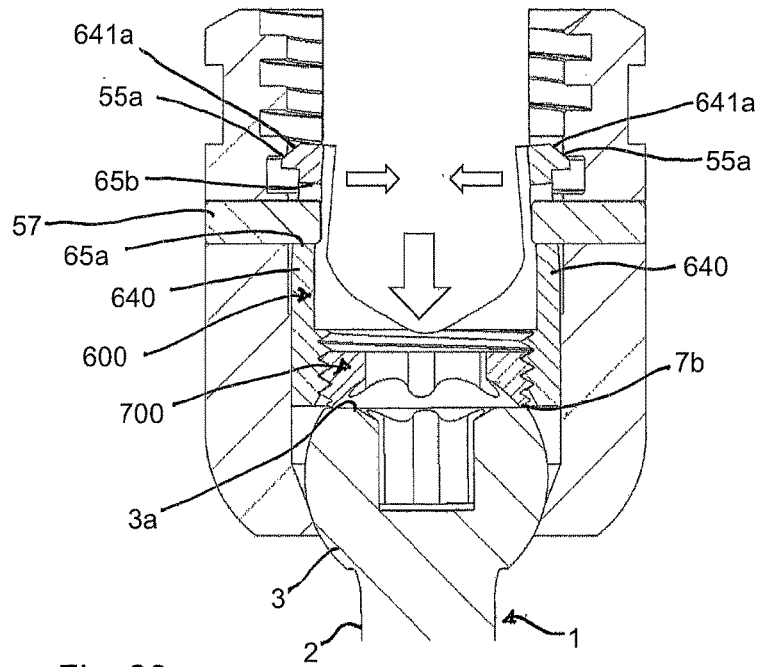

BONE ANCHORING DEVICE

CROSS-REFERENCE TO RELATED APPLICATION(S)

The present application claims priority to and the benefit of U.S. Provisional Patent Application No. 62/893,998, filed Aug. 30, 2019, the contents of which are hereby incorporated by reference in their entirety, and claims priority from European Patent Application EP 19 194 781.1, filed Aug. 30, 2019, the contents of which are hereby incorporated by reference in their entirety.

BACKGROUND

Field

The application relates to a bone anchoring device of the polyaxial type that includes a receiving part and a bone anchor with a shank, which permits a provisional clamping and/or locking of an angular position of the shank relative to the receiving part without a rod being inserted. The bone anchoring device is particularly applicable in spinal surgery.

Description of Related Art

Some pedicle screws or other bone anchoring devices permit temporary clamping of a head of an anchoring screw relative to a receiving part before final locking. Due to the necessity in some situations to correct a position of the receiving part of the bone anchoring device relative to the anchoring screw, in some cases it may be desirable to perform such correction steps without a spinal rod being received in the receiving part.

In U.S. Pat. No. 5,443,467 a bone anchoring device in the form of a polyaxial bone screw is described, that includes a screw member, the head of which is pivotably received in a receiver member. A head locking nut is provided which can be screwed into the receiver member towards the head. Once the position of the receiver member is adjusted for receiving the rod to be connected with the bone screw, the head locking nut is tightened to such an extent that the screw member is rigidly connected to the receiver member. Thereafter, the rod is inserted into a U-shaped recess of the receiver member and positionally locked by inserting and tightening a rod locking nut.

U.S. Pat. No. 9,839,446 B2 describes a coupling device for coupling a rod to a bone anchoring element. The coupling device includes a receiving part defining an accommodation space for accommodating a head of the bone anchoring element. Further, the coupling device includes a pressure element with a flexible portion to clamp a head inserted therein and a clamping element configured to exert a compression force onto the pressure element to increase a friction force between the pressure element and the head. The compression force onto the head can be adjusted before a rod is inserted.

SUMMARY

It is an object of the invention to provide an improved or alternative bone anchoring device that permits adjustment of a position of a receiving part relative to a shank of a bone anchoring element, and provisionally holding such an adjusted position without a rod being inserted into the receiving part.

By integrating an insert member with a pressure member that can be actuated separately from the pressure member, it is possible to temporarily or provisionally lock an angular position of the shank relative to the receiving part when a rod is not inserted into the receiving part. Also, the temporary locking can be released to permit further positional correction.

The strength of the temporary locking can be adjusted by varying a position (e.g., an axial position) of the insert member to create an adjustable pressure onto a head of the bone anchoring element. Hence, the insert member can exert a force onto the head, such that the head is held by friction in an angular position and can be pivoted by overcoming the frictional force. When the force exerted by the insert member is increased, the head can be provisionally locked.

With the aid of a separate locking member that acts directly or via the rod onto the pressure member, the bone anchoring device can be finally locked, for example, with an increased locking force compared to the provisional locking.

The polyaxial bone anchoring device may be of the top-loading type, wherein the bone anchoring element is inserted through a top end of the receiving part. Or the polyaxial bone anchoring device may be of the bottom-loading type, wherein the bone anchoring element is inserted into the receiving part from a bottom end thereof.

According to a further embodiment, a head contacting surface portion of the insert member can have a shape that cooperates with the head in a form-fit manner, so that the bone anchoring element can assume a single angular position, for example, a zero angle position, relative to the receiving part, where the respective central axes of the bone anchoring element and the receiving part are substantially aligned or coaxial. Thus, a monoaxial bone anchoring device can be provided.

According to a still further embodiment, a head contacting surface portion of the insert member can have a shape that cooperates with the head of the bone anchoring element in a manner such that the bone anchoring element is held by the compression force exerted by the insert member onto the head in a single angular position, for example in the zero angle position, to provide a monoaxial bone anchoring device.

In a still further embodiment, the insert member has a head contacting surface that cooperates with the head in such a manner that a specific angular position of the bone anchoring element relative to the receiving part can be indicated and/or verified. A feedback may be given to a user when the specific angular position is achieved or moved away from. This may be particularly useful in cases in which high angles of the shank relative to the receiving part are needed.

According to a still further embodiment, a kit includes a receiving part, a bone anchoring element, a pressure member, and at least two insert members that can be interchangeably connected to the pressure member. One of the insert members may be configured to cooperate with the head of the bone anchoring element to allow pivoting of the head. Another one of the insert members may be configured to cooperate with the head to provide a monoaxial bone anchoring device. Hence, the flexibility or variety of implants that is easily available to a surgeon can be increased by providing a modular system with various insert members that can be combined with one pressure member.

Generally, a polyaxial bone anchoring device according to embodiments of the invention largely broadens the range of applications, as it provides a greater variety of adjustable locking functions.

BRIEF DESCRIPTION OF THE DRAWINGS

Further features and advantages will become apparent from the detailed description of embodiments by means of the accompanying drawings. In the drawings:

FIG. 1 shows an exploded perspective view of a bone anchoring device according to a first embodiment of the invention, with a rod and a locking member.

FIG. 2 shows a perspective view of the bone anchoring device of FIG. 1 in an assembled state with the rod and the locking member.

FIG. 12 shows a perspective view from a top of an insert member that is positionable at least partially in the pressure member of FIGS. 8 to 11.

FIG. 13 shows a perspective view from a bottom of the insert member of FIG. 12.

FIG. 14 shows a top view of the insert member of FIGS. 12 and 13.

FIG. 15 shows a cross-sectional view of the insert member of FIGS. 12 to 14, the cross-section taken along line D-D in FIG. 14.

FIGS. 16a and 16b show cross-sectional views of modified insert members according to two alternative embodiments.

FIGS. 17a to 17e show steps of assembling and using the bone anchoring device according to the first embodiment.

FIG. 18a shows a cross-sectional view of the bone anchoring device according to the first embodiment in a configuration where the receiving part is freely pivotable relative to a shank of the bone anchoring element.

FIG. 18b shows an enlarged portion of FIG. 18a.

FIG. 19a shows a cross-sectional view of the bone anchoring device according to the first embodiment in a configuration where the insert member is exerting pressure onto the head.

FIG. 19b shows an enlarged view of a detail of FIG. 19a.

FIGS. 28a to 28c show cross-sectional views of steps of using the polyaxial bone anchoring device according to the second embodiment to indicate a pre-defined shank position.

FIGS. 29a to 29c show cross-sectional views of steps of using the polyaxial bone anchoring device according to the second embodiment as a monoaxial bone anchoring device.

DETAILED DESCRIPTION

Figure 3:
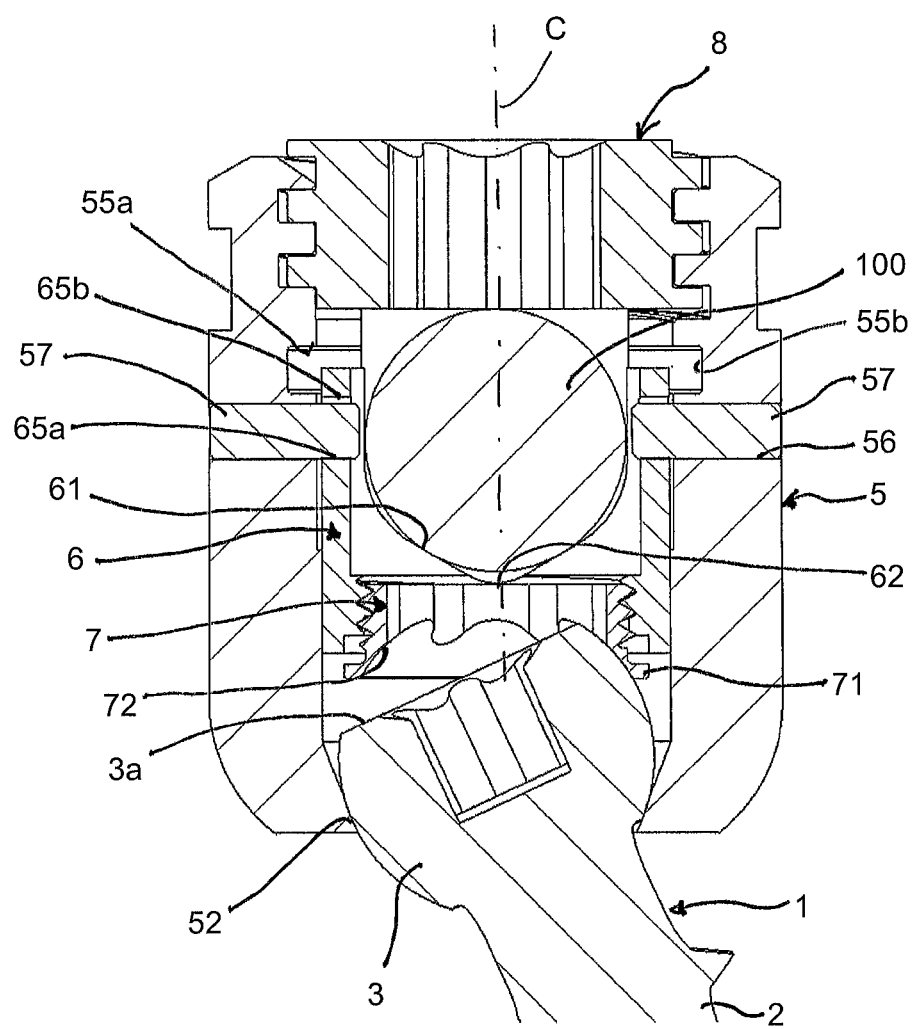
FIG. 3 shows a cross-sectional view of the bone anchoring device of FIGS. 1 and 2, the cross-section taken in a plane extending through a center of the receiving part and perpendicular to an inserted rod.
Figure 4:
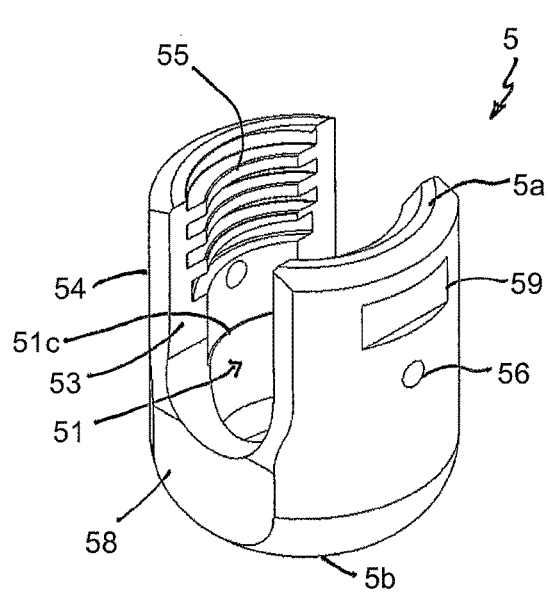
FIG. 4 shows a perspective view from a top of a receiving part of the bone anchoring device of FIGS. 1 to 3.
Figure 5:
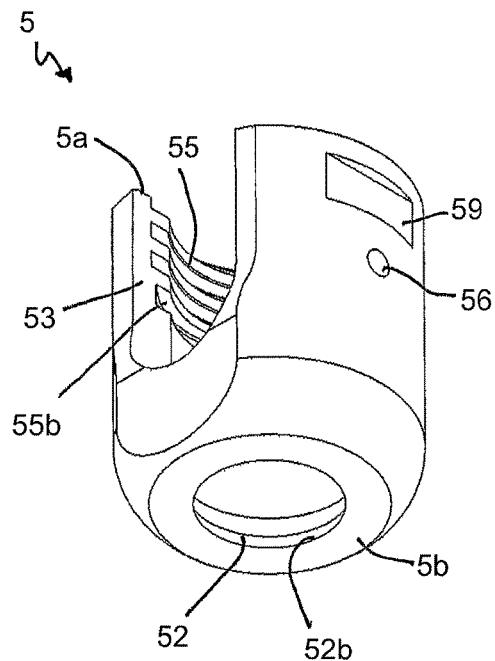
FIG. 5 shows a perspective view from a bottom of the receiving part of FIG. 4.
Figure 6:
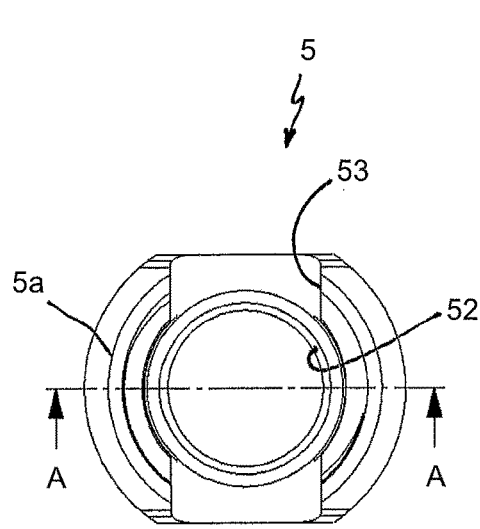
FIG. 6 shows a top view of the receiving part of FIGS. 4 and 5.
Figure 7:
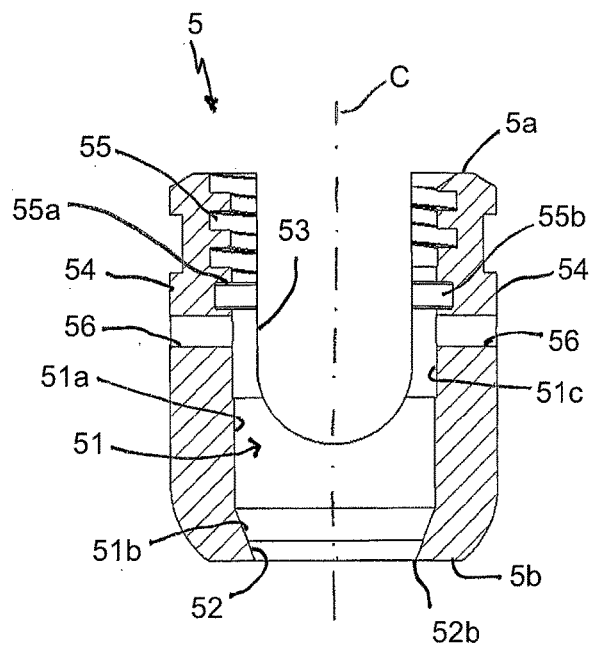
FIG. 7 shows a cross-sectional view of the receiving part of FIGS. 4 to 6, the cross-section taken along line A-A in FIG. 6.
Figure 8:
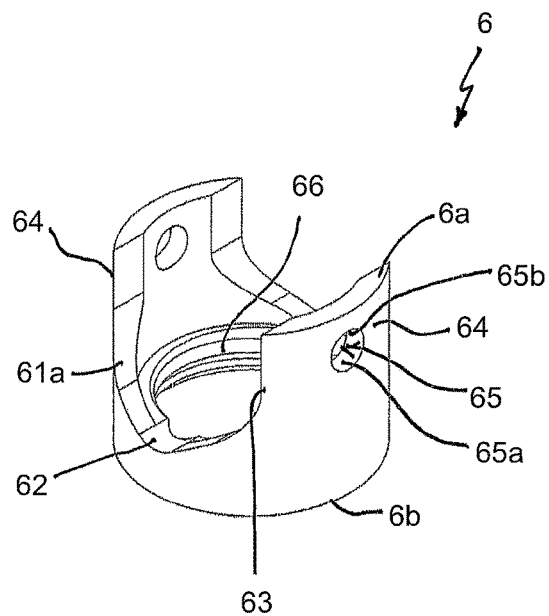
FIG. 8 shows a perspective view from a top of a pressure member of the bone anchoring device of FIGS. 1 to 3.
Figure 9:
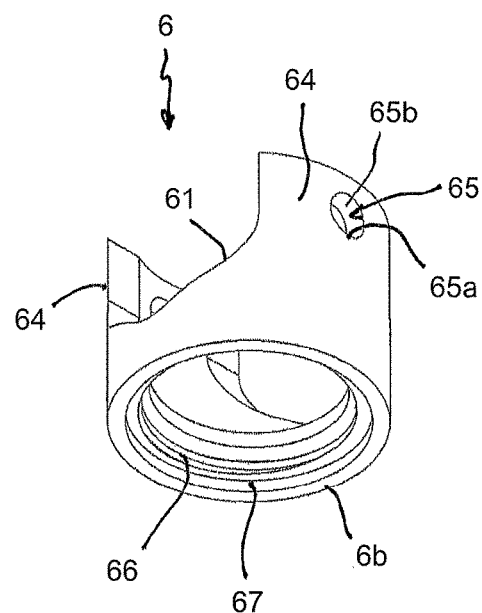
FIG. 9 shows a perspective view from a bottom of the pressure member of FIG. 8.
Figure 10:
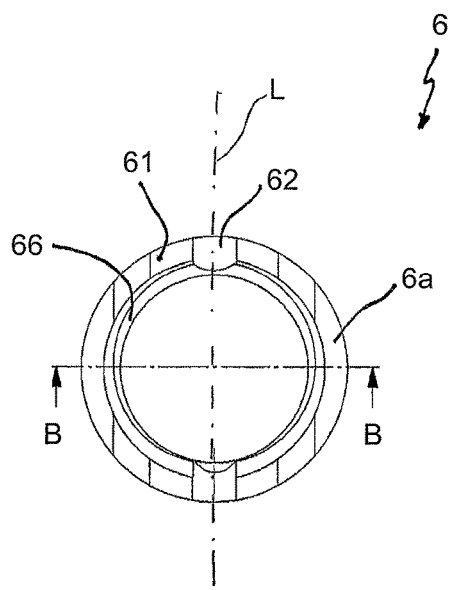
FIG. 10 shows a top view of the pressure member of FIGS. 8 and 9.
Figure 11:
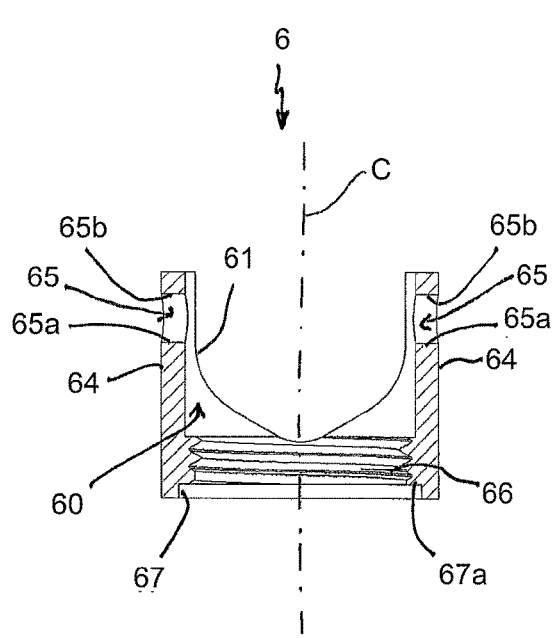
FIG. 11 shows a cross-sectional view of the pressure member of FIGS. 8 to 10, the cross-section taken along line B-B in FIG. 10.
Figure 20:
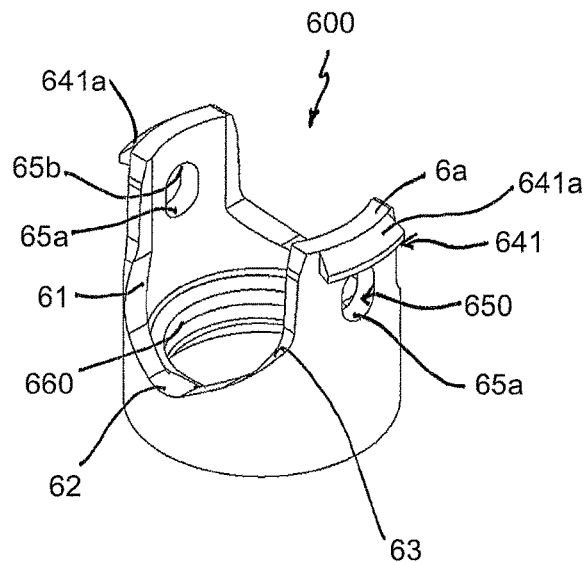
FIG. 20 shows a perspective view from a top of a pressure member of a second embodiment of the polyaxial bone anchoring device.
Figure 21:
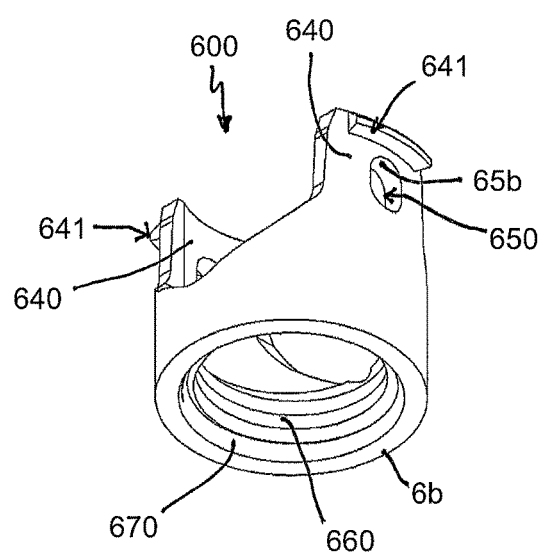
FIG. 21 shows a perspective view from a bottom of the pressure member of FIG. 20.
Figure 22:
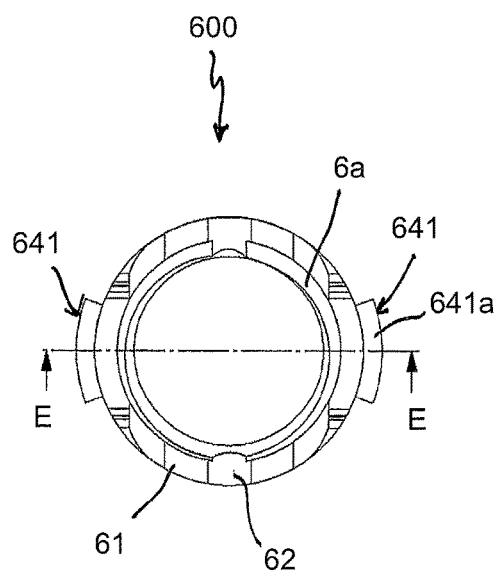
FIG. 22 shows a top view of the pressure member of FIGS. 20 and 21.
Figure 23:
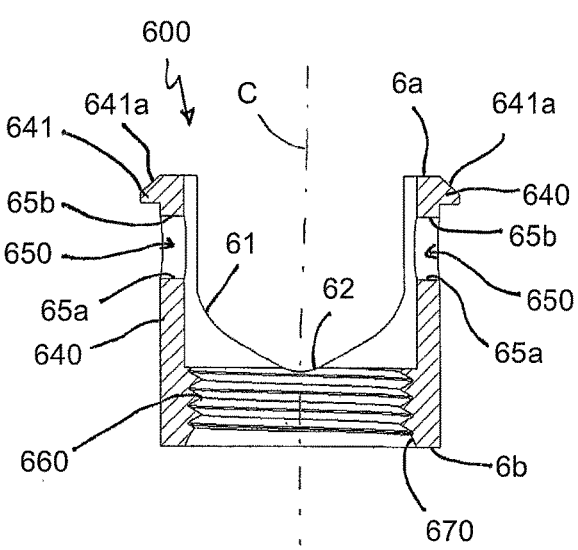
FIG. 23 shows a cross-sectional view of the pressure member of FIGS. 20 to 22, the cross-section taken along line E-E in FIG. 22.
Figure 24:
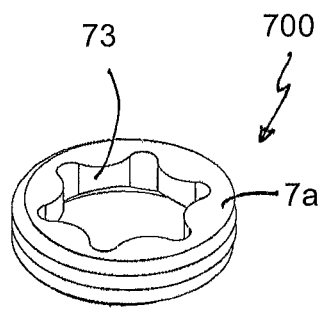
FIG. 24 shows a perspective view from a top of an insert member of the second embodiment of the polyaxial bone anchoring device.
Figure 25:
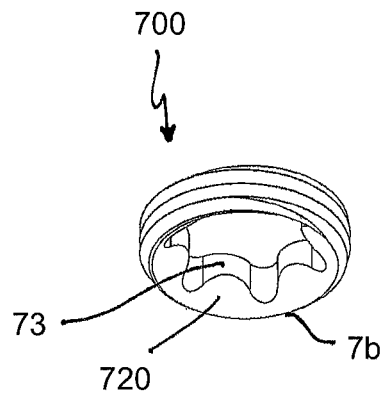
FIG. 25 shows a perspective view from a bottom of the insert member of FIG. 24.
Figure 26:
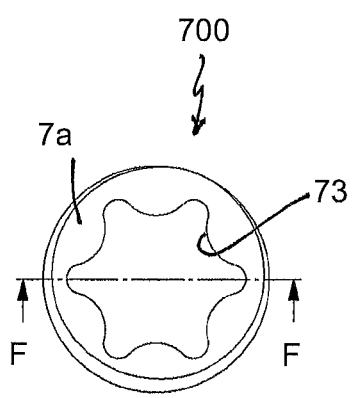
FIG. 26 shows a top view of the insert member of FIGS. 24 and 25.
Figure 27:
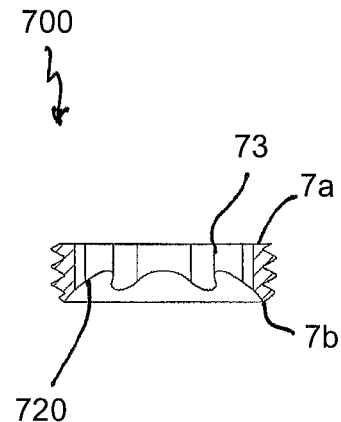
FIG. 27 shows a cross-sectional view of the insert member of FIGS. 24 to 26, the cross-section taken along line F-F in FIG. 26.

A polyaxial bone anchoring device according to a first embodiment, which is generally shown in FIGS. 1 to 3, includes a bone anchoring element 1 in the form of a screw member having a shank 2 which is at least partially threaded and a head 3. The head 3 has a spherical outer surface portion. In greater detail, in the first embodiment, the head 3 is shaped as a spherical segment with a substantially flat end surface 3a in which a recess 4 for engagement with a tool may be provided. The bone anchoring device further includes a receiving part 5 for connecting the bone anchoring element 1 to a rod 100. In the receiving part 5, a pressure member 6 can be inserted that is configured to exert pressure onto the head 3. An insert member 7 is arranged at least partially in the pressure member 6 at a side facing towards the head 3. The insert member 7 is configured to come into contact with the head 3 to exert pressure directly onto the head 3. For securing the rod 100 in the receiving part 5, and for exerting pressure onto the head 3 to finally lock the head 3 in some embodiments, a locking member 8 in the form of, for example, a set screw which cooperates with the receiving part 5 may be provided. The locking member 8 may have a tool engagement recess 8a.

As shown in particular in FIGS. 3 to 7, the receiving part 5 is substantially cylindrical, and has a first end or top end 5a, a second end or bottom end 5b, and a passage 51 extending from the top end 5a towards the bottom end 5b and defining a longitudinal central axis C. At the bottom end 5b, a seat portion 52 is formed for accommodating the head 3. The seat portion 52 is configured to permit the head 3 to pivot therein, similar to a ball and socket joint. The seat portion 52 may be spherically-shaped corresponding to the spherical shape of the head 3, or may have any other shape that allows the head to pivot, such as, for example, a conically tapering shape. The seat portion 52 is in communication with the passage 51 and has an opening 52b through which the shank 2 of the bone anchoring element 1 can extend. An inner diameter of the opening 52b is smaller than a greatest diameter of the head, so that the bone anchoring element 1 is insertable only from the top end 5a into the receiving part 5. Hence, the first embodiment shows a top-loading polyaxial bone anchoring device. The passage 51 has a central section 51a with an inner width that is greater than the greatest diameter of the head, for example, to provide space for the pressure member 6 and the insert member 7. Further, the passage 51 narrows towards the seat at a narrowing portion 51b. Above the central section 51a, there may be a slightly wider section 51c with an increased diameter compared to the central section 51a.

A substantially U-shaped recess 53 extends from the top end 5a to a distance therefrom. The substantially U-shaped recess 53 divides the upper portion of the receiving part 5 into two free legs 54 and forms a channel for receiving the rod 100. An internal thread 55, for example a square thread, is provided at the receiving part 5 adjacent to the top end 5a for cooperating with the locking member 8. At the end of the internal thread, there may be an undercut 55b. In the center of the legs 54 in a circumferential direction, through-holes 56 extend through the wall of the legs with a longitudinal axis that may be perpendicular to the central axis C. The through-holes 56 serve for receiving pins 57 that extend in a mounted state into the passage 51 to form an abutment, as described in greater detail below. The through-holes 56 may be located below the internal thread 55 and above a bottom of the U-shaped recess 53.

Optionally, cutouts 58 may be formed on either side of the legs 54 on the receiving part 5, which may contribute to a reduced size of the receiving part. Lastly, optionally tool engagement portions 59, such as a circumferential groove provided at the outer wall of the legs 54, allow engagement of the receiving part 5 with a tool.

Next, the pressure member 6 will be described with reference to FIGS. 1 to 3 and 8 to 11. The pressure member 6 may be a separate, monolithic piece having a substantially cylindrical outer shape, with a first end or top end 6a and an opposite second end or bottom end 6b. A coaxial passage 60 extends from the top end 6a to the bottom end 6b, and which may be formed in a first section adjacent to the top end 5a as an unthreaded bore. The pressure member 6 is mounted in the receiving part 5 in a manner such that the bottom end 6b faces towards the head 3. A recess 61 is formed that extends from the top end 6a to a distance therefrom towards the bottom end 6b, and has a longitudinal axis L that is perpendicular to a cylinder axis C of the pressure member 6, the latter of which coincides with the central axis C of the receiving part 5 when the pressure member 6 is in the receiving part 5. The recess 61 has a generally V-shaped contour. This permits rods 100 having different diameters to be more effectively received in the recess 61.

The lateral edges 61a and the bottom 62 of the generally V-shaped recess 61 may be rounded. Moreover, upstanding legs 64 are formed by the generally V-shaped recess 61, and optionally lateral cut-outs 63 may be provided so that the legs 64 have a reduced width in a circumferential direction. The legs 64 may have a height, or in other words, the generally V-shaped recess 61 has a depth, such that the top end 6a of the pressure member is below the highest point of the surface of an inserted rod 100 for any rod diameter that can be safely received in the generally V-shaped recess 61. At the center of each of the legs 64 in a circumferential direction, transverse through-holes 65 are provided that extend through the legs 64 perpendicular to the longitudinal axis L and perpendicular to the cylinder axis C of the pressure member 6. The through-holes 65 have a width such that they can receive the pins 57. In an axial direction parallel to the cylinder axis C, a height of the through-holes 65 is greater than a diameter of the pins 57, such that the pins are movable in the through-holes 65 in the axial direction to some extent. Hence, a lower end 65a of each through-hole in the axial direction parallel to the cylinder axis C of the pressure member 6 forms a first abutment for the pins 57, and a top end 65b of each through-hole 65 forms a second abutment for the pins 57.

Between approximately the bottom 62 of the V-shaped recess and the bottom end 6b, the passage 60 has an internally threaded section 66 that is configured to house and engage the insert member 7. The thread forms an advancement structure to permit an adjustable advancement of the insert member 7. An internal diameter of the internally threaded section 66 may be the same or smaller than that of the upper portion of the passage 60, so that the insert member can extend into the upper portion of the passage 60 when the insert member is fully screwed into the pressure member 6 (shown, for example, in FIGS. 17b, 18a, and 18b). Adjacent to the bottom end 6b, a cylindrical recess 67 is formed in the pressure member 6, an inner diameter of which is greater than the inner diameter of the internally threaded section 66, such that an abutment shoulder 67a is formed for a portion of the insert member 7. As best seen in FIG. 3, an outer diameter of the pressure member 6 is such that the pressure member is only slightly smaller than an inner diameter of the passage 51. By means of this, the pressure member 6 can slide or can be displaced axially in the passage 51 of the receiving part 5. An axial length of the pressure member along the central axis C is such that, as seen in FIG. 3, when the pressure member 6 is mounted to the receiving part 5 and receives the pins 57 in the through-holes 65, the insert member 7 can be advanced to contact the head 3 and can be retracted to get out of contact with the head 3.

The insert member 7 will be explained, referring in greater detail to FIGS. 1 to 3 and 12 to 15. The insert member 7 is substantially a set-screw like member and has a first end or top end 7a and a second end or bottom end 7b.

When the insert member 7 is assembled with the pressure member 6, the top end 7a of the insert member faces towards the top end 6a of the pressure member 6. At the bottom end 7b, a circumferentially extending radial projection 71 is formed that fits in an assembled state into the cylindrical recess 67 of the pressure member 6. Thereby, the shoulder 67a onto which an upper surface of the projection 71 abuts, forms a stop for the insert member 7 in the pressure member 6. This prevents loss of the insert member through the top end 6a of the pressure member 6. The outer surface of the insert member 7 is threaded above the radial projection 71. Furthermore, on the bottom end 7b, a spherically-shaped recess 72 is formed that matches the shape of the spherical outer surface portion of the head 3. The spherically-shaped recess 72 has a size such that it is configured to cover at least a portion of the spherically-shaped outer surface portion of the head 3 when the pressure member 6 and the insert member 7 are at their lowermost positions in the receiving part 5. Lastly, a tool engagement recess 73 is provided at the top end 7a. The tool engagement recess 73 extends fully through the insert member 7 in the axial direction. Hence, a portion of the head 3 can extend therein when the head pivots at larger angles relative to the receiving part. The tool engagement recess 73 may have any shape suitable for engagement with a tool, such as a polygon shape or a torx-like or star-like shape.

Turning now to FIGS. 16a and 16b, modifications to the insert member 7' are shown in FIG. 16a that result in the insert member 7' and the head 3 entering into a form-fit connection. In FIG. 16a, the spherical recess 72 continues into a flat cover portion 74, providing an edge 74a so that the flat cover portion 74 and the spherical recess 72 cooperate with the end surface 3a and the spherical surface portion of the head 3 in a form-fit manner. Thus, the insert member 7' is configured to cooperate with the head 3 in such a manner that the shank 2 assumes a zero angle relative to the receiving part 5, where a longitudinal axis of the shank is substantially coaxial or aligned with the thread axis of the insert member 7', which in turn is coincident with the central axis C of the receiving part 5 (i.e., where the longitudinal axis of the shank is substantially coaxial or aligned with the central axis C of the receiving part 5).

In FIG. 16b, a further modified insert member 7" is shown which has, in addition to the flat cover portion 74 and extending from the same one or more annular projections 74b that can cooperate with corresponding grooves of the head 3 (not shown) to strengthen the form-fit connection.

The parts and portions of the bone anchoring device may be made of any material, preferably however, of titanium or stainless steel or of any bio-compatible metal or metal alloy or plastic material. For a bio-compatible alloy, a NiTi alloy, for example Nitinol, may be used. Other materials that can be used are magnesium or magnesium alloys. Bio-compatible plastic materials that can be used may be, for example, polyether ether ketone (PEEK) or poly-L-lactide acid (PLLA). The respective parts can be made of the same material or materials, or of different materials from another.

FIGS. 17a to 17e show steps of assembling and using the polyaxial bone anchoring device according to the first embodiment. In FIG. 17a the bone anchoring element 1 is inserted from the top end 5a of the receiving part 5, so that the shank 2 extends through the lower opening 52b and the head 3 rests in the seat 52. In FIG. 17b, the preassembled pressure member with insert member 7 is mounted from the top end 5a into the receiving part 5. The insert member 7 abuts with the radial projection 71 against the edge 67a in the pressure member 6 (see in greater detail in FIGS. 18a and 18b). The top end 7a of the insert member 7 extends into the upper portion of the passage 60 of the pressure member 6. In FIG. 17c, the pins 57 can be inserted and positioned to extend through the through-holes 56 of the receiving part 5 into the through-holes 65 of the pressure member 6, so that the V-shaped recess 61 of the pressure member 6 is aligned with the U-shaped recess 53 of the receiving part 5. Thereby, the pressure member 6 is rotationally secured. In FIG. 17d, the insert member has been screwed downwards by engaging the tool engagement recess 73 with a tool (not shown). As a result, an outer spherical surface portion of the head 3 comes into contact with the inner wall of the spherical recess 72 of the insert member 7. In FIG. 17e, the receiving part 5 with the assembled pressure member 6 and insert member 7 can be pivoted relative to the head 3, so that the head 3 enters on one side deeper into the spherically-shaped recess 72 of the insert member 7.

In clinical use, at least two bone anchoring devices are anchored into bone parts or vertebrae. The shank is for example inserted into a prepared core hole. Then, the receiving parts 5 are aligned to have a corrected or desired orientation for insertion of the rod 100.

FIGS. 18a to 19b show in greater detail the function of the insert member 7. In FIGS. 18a and 18b, the pins 57 engage the upper ends 65b of the through-holes 65 and the insert member 7 is fully screwed into the pressure member 6. In this configuration, the shank 2 and the head 3 are freely pivotable in the seat 52. In FIGS. 19a and 19b, the insert member 7 is screwed downward towards the head 3. This can be achieved by engaging the tool engagement recess 73 with a tool through the access opening provided by the passage 60 in the pressure member 6. As soon as the inner surface of the spherically-shaped recess 72 of the insert member 7 contacts the head 3, a counterforce is generated that slightly moves the pressure member 6 towards the top end 5a of the receiving part 5 until the lower ends 65a of the through-holes 65 abut against the pins 57, respectively. The pins, in turn, generate a counterforce that acts back onto the insert member and the head. By means of this, an adjustable pressure can be exerted by the insert member 7 onto the head 3 depending on how much the insert member 7 is tightened towards the head 3. Hence, it is possible to achieve a friction-fit hold on the head 3, which means that the head 3 is held in an adjustable angular position by a friction force. Here, the angular position of the head can still be changed by moving the receiving part 5, for example manually, relative to the head to overcome the friction force. On the other hand, if the insert member 7 is fully tightened against the head 3, the friction force is strong enough that a provisional locking of the head 3 in a desired angular position can be achieved.

The friction-fit hold of the head 3 or the provisional locking of the head 3 can both be released by screwing the insert member 7 backwards into the pressure member 6. The generation of the friction-fit hold and/or the provisional locking of the head and the release thereof can be carried out without a rod being received in the receiving part and the pressure member, in other words, when the rod receiving recess is unobstructed. The steps of generating a friction-fit and/or a provisional locking can be carried out multiple times. Hence, multiple adjustment steps can be carried out easily.

A modular system can be provided that includes the receiving part, the pressure member, and at least two of the insert members, wherein one of the insert members allows pivoting of the head as described above and another one of the insert members is configured to lock the zero angular position of the shank when the insert member engages the head.

Lastly, the rod 100 can be inserted and the locking member 8 can then be inserted and tightened until the locking member 8 exerts a pressure onto the rod 100, which in turn exerts a pressure onto the pressure member 6, such that the head 3 is finally locked in the receiving part 5. By the final locking via the locking member, an increased locking force can be achieved, which may be more suitable for a permanent locking of the device.

A second embodiment of the bone anchoring device will be described with reference to FIGS. 20 to 30*b*. The bone anchoring device of the second embodiment differs from the bone anchoring device of the first embodiment in the design of the pressure member and of the insert member. Portions that are identical or substantially similar to portions of the first embodiment are indicated with the same reference numerals, and the descriptions thereof will not be repeated. The pressure member 600 of the second embodiment has upstanding legs 640 that are slightly longer compared to the legs in the first embodiment. At the top end 6*a* of each leg 640, there is a circumferentially and radially outward extending projection 641. In the circumferential direction, the projection may extend to a distance from the lateral edges of each leg 640. The projection 641 has an upper inclined surface 641*a* that is configured to abut against an abutment in the form of an upper edge 55*a* of an undercut 55*b* of the receiving part 5 (see FIGS. 28*a* to 30*b*). Due to their shape and size, the legs 640 are slightly flexible in such a manner that the legs 640 can be elastically bent radially inward and can snap or move back to a straight position. The widened portion 51*c* of the passage in the receiving part provides additional space for the legs. The through-holes 650 are elongate in the axial direction, extending parallel to the cylinder axis C, to provide slightly increased axial freedom for displacing the pressure member 600 in the receiving part 5. As can best be seen in FIG. 28*a*, the legs 640 have a length such that they touch the upper edge 55*a* of the undercut 55*b* when the pressure member 600 with the assembled insert member 700 is in the receiving part 5 and the pins 57 abut against the upper end 65*b* of the through-holes 650. The radial projections 641 can extend into the undercut 55*b*. In this position, the head 3 is freely pivotable.

The pressure member 600 further has, at the second end 6*b*, a conical recess 670 which widens towards the second end 6*b*. An inner diameter of the threaded section 660 of the passage 600 is the same or is preferably smaller than the diameter of the flat end surface 3*a* of the head 3. Hence, the dimensions of the threaded section 660 of the passage and of the widening recess 670 are such that the head 3 may enter into the widening recess 670, but not significantly into the threaded section 660.

Turning now to FIGS. 24 to 27, the insert member 700 is a set screw that is configured to be screwed into the threaded section 660 of the pressure member 600. The insert member 700 may have an axial length that corresponds substantially to the axial length of the threaded portion 660 of the pressure member 600. The spherically-shaped recess 720 at the lower end has a size configured to fit over the head 3 when the head 3 enters into the recess 720. Due to the smaller external diameter, the bottom end 7*b* of the insert member 700 is configured to rest on the flat end surface 3*a* of the head 3 when the insert member 700 comes into contact with the head 3 in the zero angle position.

FIGS. 28*a* to 28*c* show a shank position indication function of the polyaxial bone anchoring device of the second embodiment. In FIG. 28*a*, the preassembled pressure member 600 with the insert member 700 are inserted into the receiving part 5 with the head 3 resting in the seat 52. The pressure member 600 rests with the upper end 65*b* of the through-holes 650 on the pins 57. The insert member 700 is fully inserted into the pressure member 600. The dimensions are such that the insert member 700 is at least at an axial position such that the spherical recess 720 matches an outer virtual contour of the head 3 if a circle is drawn around the spherical outer surface portion of the head 3. In this configuration, the head 3 is freely pivotable in the seat 52 and can enter the recess 720 during pivoting. Thus, the shank 2 can assume various angular positions. The inclined upper surface 641 of the projection 640 touches the upper edge 55*a* of the undercut 55*b*.

FIG. 28*b* shows a configuration in which the insert member 700 is screwed down until it abuts against the end surface 3*a* of the head 3 when the shank 2 is at a zero angle position relative to the central axis C. In this position, the head 3 is slightly clamped in the zero angular position. By means of the slight clamping of the head in the zero angular position, an indication of the zero angular position is generated.

FIG. 28*c* shows a step of pivoting the receiving part 5 relative to the bone anchoring element 1 after the device assumes the position shown in FIG. 28*b*. When the head 3 pivots, the pressure member 600 with the insert member 700 is pushed slightly upward to provide space so that the head 3 can enter the spherically-shaped recess 720. The legs 640 abut with the inclined upper surfaces 641*a* of the projections 641 against the edges 55*a* and are resiliently pressed inward. By the counter-force exerted by the resilient legs 640, the pressure member 600 is slightly pressed downward to exert a frictional force onto the head 3. As a result, the head 3 is frictionally clamped between the insert member 700 and the seat 52. When the head enters the spherically-shaped recess 720 a haptic feedback may be created that indicates, that the shank 2 has left the zero angular position or a range of small angles close to the zero angular position. As the head 3 is clamped with the aid of the resilient legs 640, changes from the zero angular position to other angular positions and back to the zero angular position are possible several times, each time creating a haptic feedback to indicate whether the shank is at or near the zero angular position or not.

A function of using the polyaxial bone anchoring device according to the second embodiment as a monoaxial bone anchoring device will now be explained with reference to FIGS. 29*a* to 29*c*. In FIG. 29*a*, the bone anchoring element 1 is freely pivotable. In FIG. 29*b*, the insert member 700 is screwed downward towards the head 3 when the head 3 is in the zero angular position, until the lower end 7*b* of the insert member 700 contacts the end surface 3*a* of the head 3. As illustrated in FIG. 29*c*, tightening the insert member 700 against the head 3 results in the pressure member 600 moving upward until the pressure member 600 abuts against the pins 57. Once the insert member 700 has been tightened to this extent, the bone anchoring element 1 is locked in the zero angular position of the shank 2 relative to the receiving part (indicated by the arrows in FIG. 29*c*). Hence, the bone anchoring device functions as a monoaxial bone anchoring device when in the configuration shown in FIG. 29*c*.

Figures 30A, 30B:
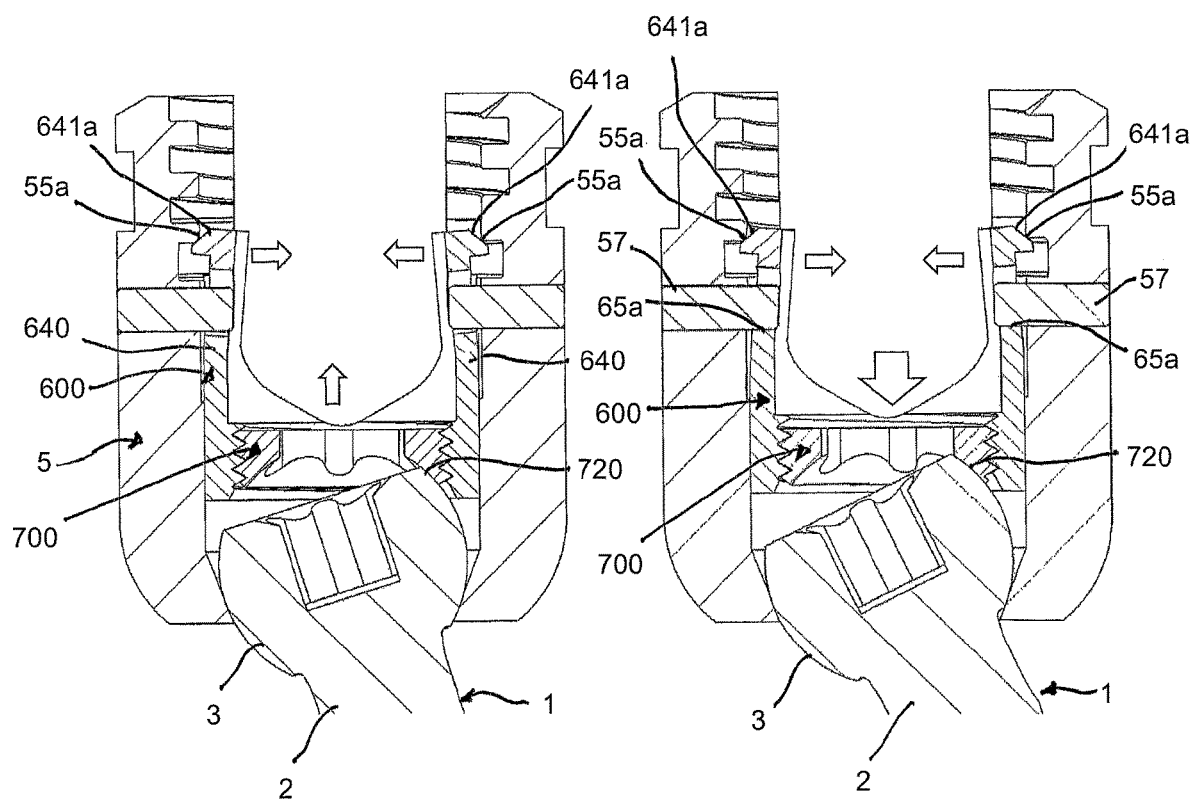
FIGS. 30a and 30b show cross-sectional views of steps of using the polyaxial bone anchoring device according to the second embodiment to provisionally lock an angular position of the shank.
Figure 31:
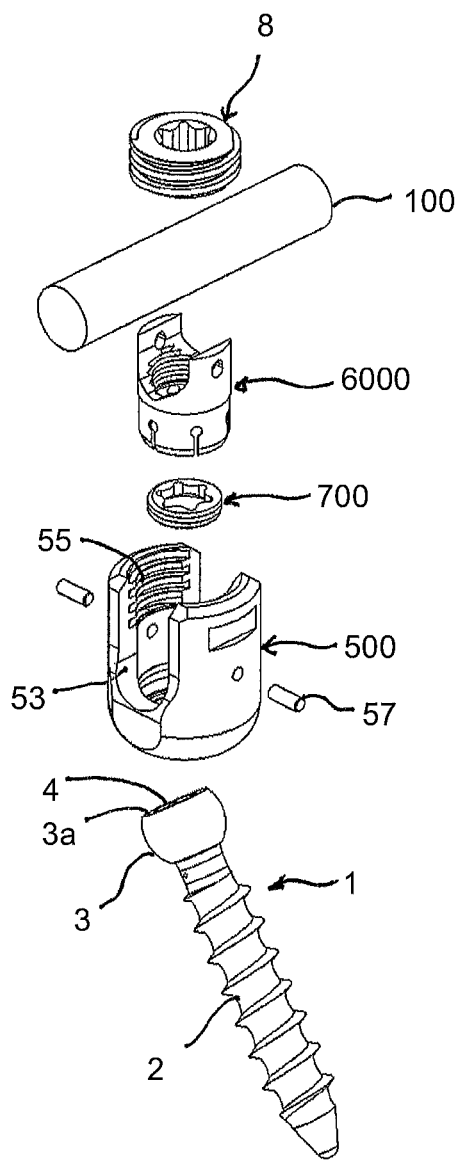
FIG. 31 shows a perspective exploded view of a polyaxial bone anchoring device according to a third embodiment, with a rod and a locking member.
Figure 32:
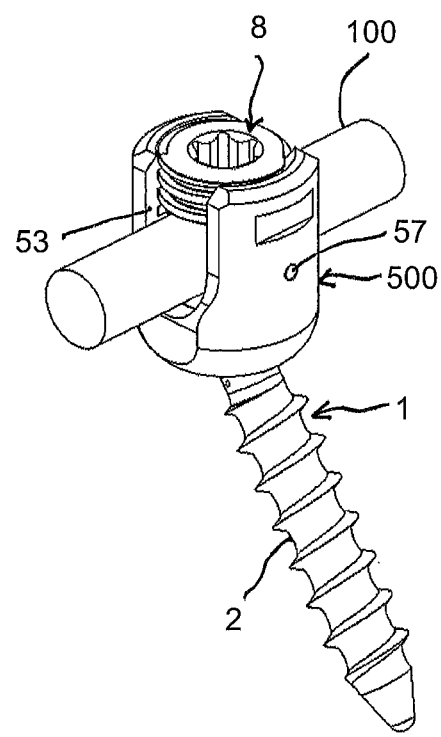
FIG. 32 shows a perspective view of the polyaxial bone anchoring device of FIG. 31 in an assembled state with the rod and the locking member.
Figure 33:
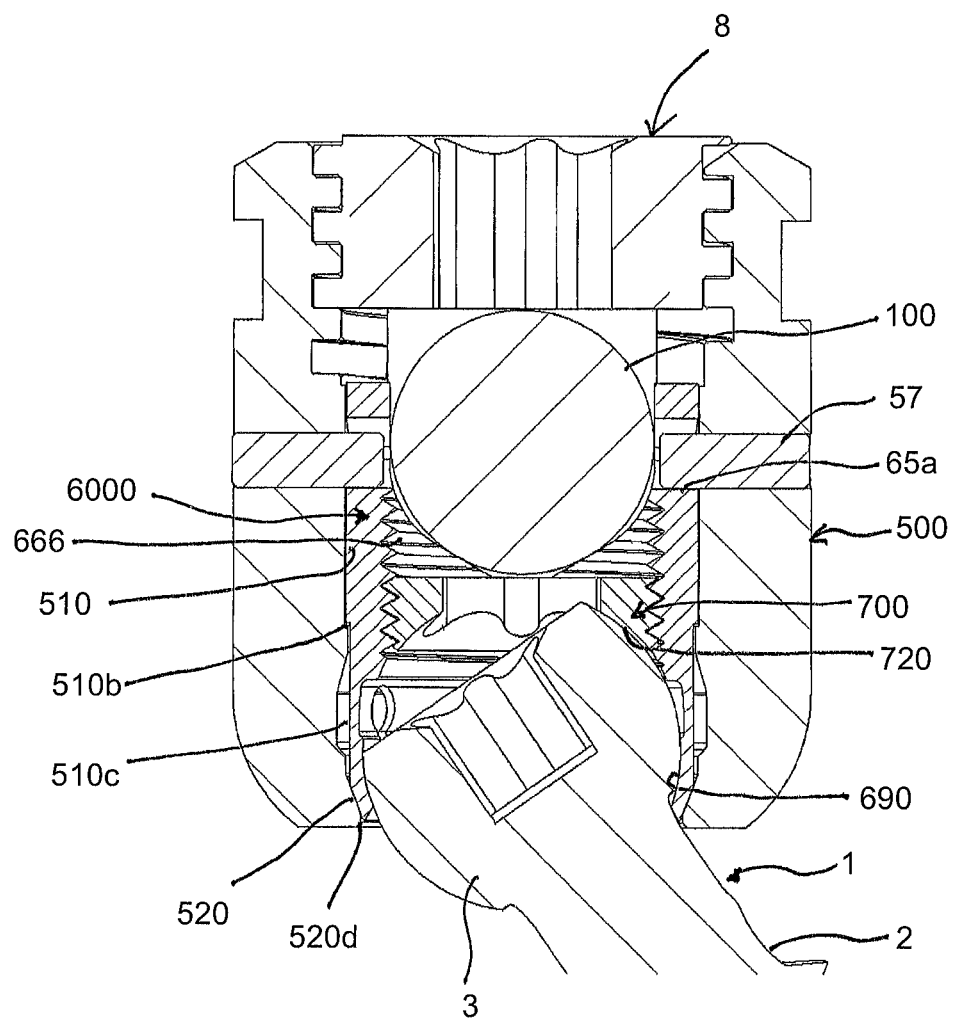
FIG. 33 shows a cross-sectional view of the polyaxial bone anchoring device of FIGS. 31 and 32, the cross-section taken in a plane extending through a center of the receiving part and perpendicular to an inserted rod.
Figure 34:
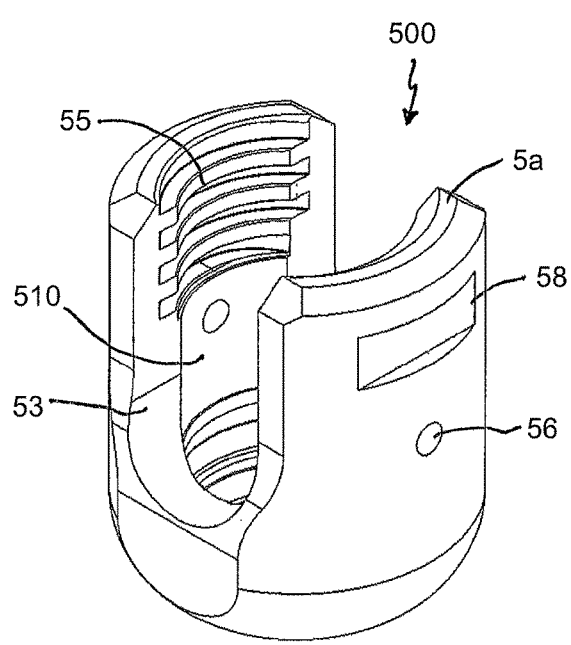
FIG. 34 shows a perspective view from a top of a receiving part of the polyaxial bone anchoring device according to the third embodiment in FIGS. 31 to 33.
Figure 35:
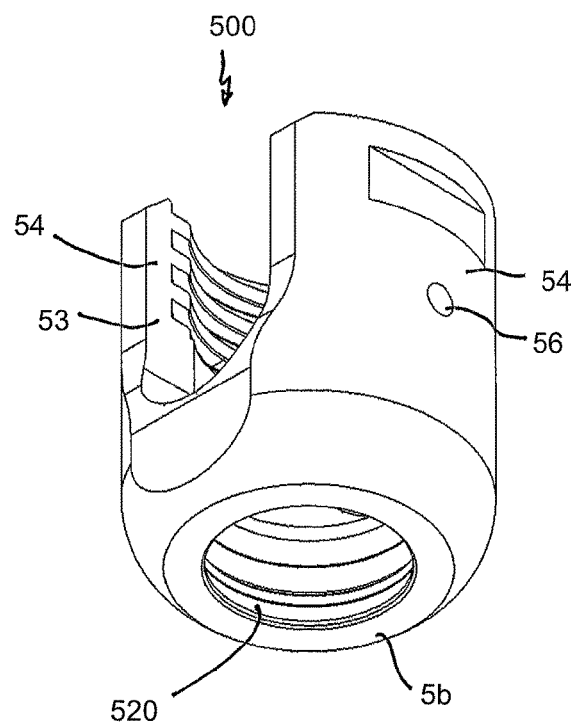
FIG. 35 shows a perspective view from a bottom of the receiving part of FIG. 34.
Figure 36:
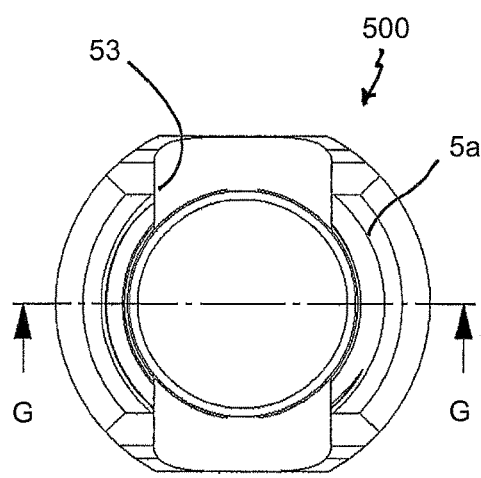
FIG. 36 shows a top view of the receiving part of FIGS. 34 and 35.
Figure 37:
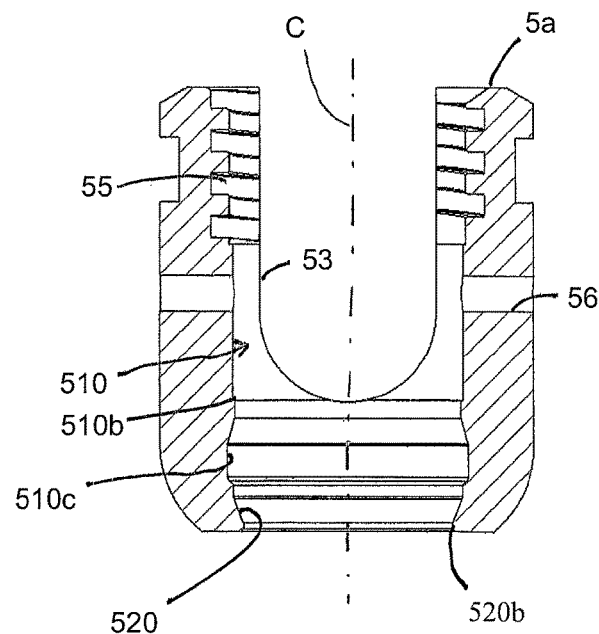
FIG. 37 shows a cross-sectional view of the receiving part of FIGS. 34 to 36, the cross-section taken along line G-G of FIG. 36.
Figure 38:
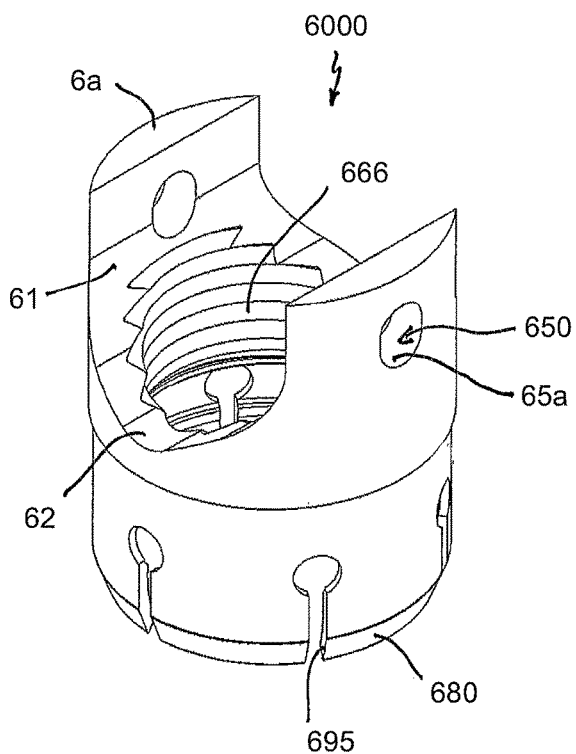
FIG. 38 shows a perspective view from a top of a pressure member of the polyaxial bone anchoring device of FIGS. 31 to 33.
Figure 39:
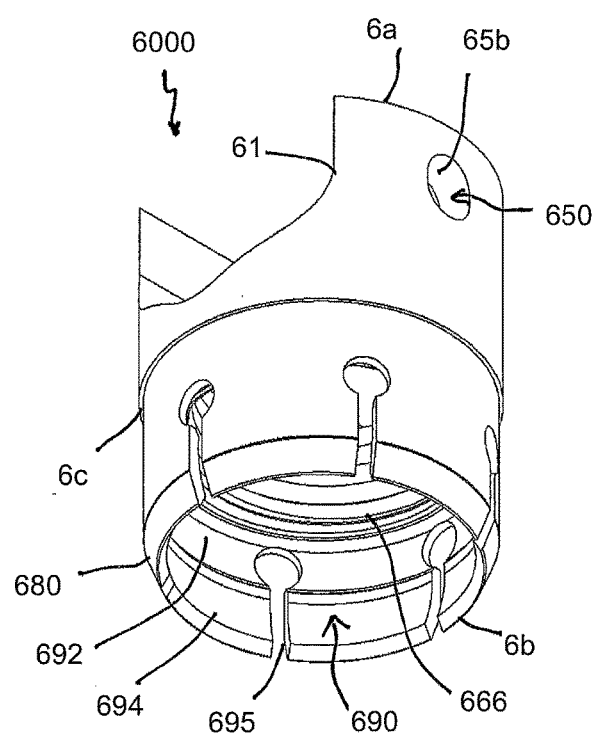
FIG. 39 shows a perspective view from a bottom of the pressure member of FIG. 38.
Figure 40:
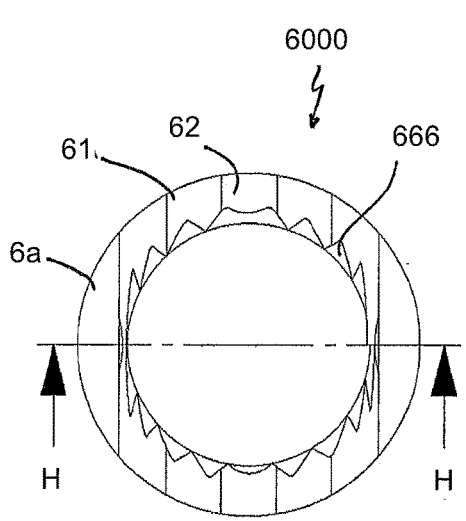
FIG. 40 shows a top view of the pressure member of FIGS. 38 and 39.
Figure 41:
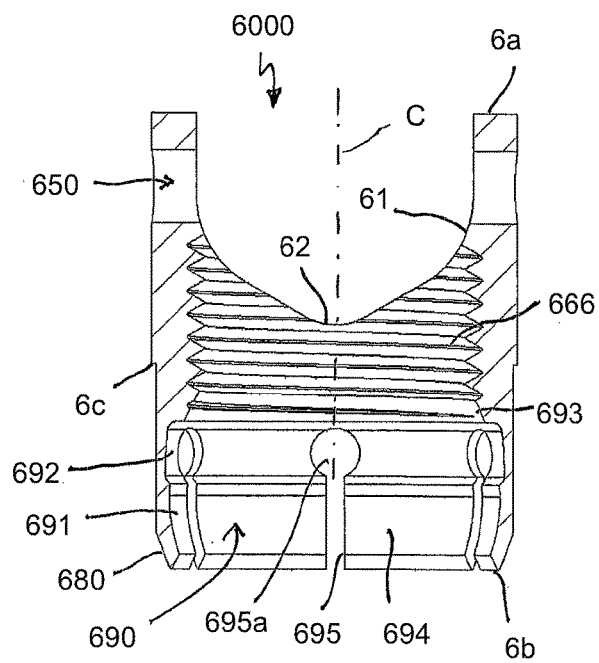
FIG. 41 shows a cross-sectional view of the pressure member of FIGS. 38 to 40, the cross-section taken along line H-H in FIG. 40.

Referring to FIGS. 30*a* and 30*b*, the provisional locking function of the polyaxial bone anchoring device of the second embodiment is shown. In the configuration shown in FIG. 30*a*, the bone anchoring element 1 is pivoted. Thereby, the pressure member is pushed slightly upwards until the flexible arms 640 are pressed inward by the increasing pressure acting by the edge 55a onto the inclined surface 641a of the projection 641 (shown by the arrows in FIG. 30a). The head 3 is held in the pivot position by the frictional force exerted by the insert member 700. In the configuration shown in FIG. 30b, the pivot position of the bone anchoring element 1 is provisionally locked by further screwing the insert member 700 downward so that the insert member 700 presses firmly onto the head 3 (indicated by the arrows in FIG. 30b).

Finally, the rod can be inserted and the locking member can then be inserted and tightened to achieve final locking of the whole construct.

A third embodiment of the bone anchoring device will be described with reference to FIGS. 31 to 42b. The bone anchoring device of the third embodiment includes an insert member 700 that is identical to that of the second embodiment. The pressure member and the receiving part of the third embodiment have a modified design, so that the bone anchoring device is of the bottom-loading type. Parts and portions that are identical or substantially similar to the first and second embodiments have the same reference numerals, and the descriptions thereof shall not be repeated.

The receiving part 500, as shown in FIGS. 31 to 37 in greater detail, has a seat portion 520 that tapers and narrows towards the second end 5b, for example, in a conical shape. By means of this, a compression force onto a portion of the pressure member 6000 can be generated, where the pressure member extends into the narrowing portion 520. Adjacent to the narrowing portion 520, a widened section 510c of the passage 510 is formed in the inner wall of the receiving part 500 in order to provide space for expansion of the pressure member 6000. A step 510b may be formed by a diameter change in the passage 510, and may serve as a stop for the insertion of the pressure member 6000. The lower opening 520b of the receiving part 500 has a width that is greater than the maximum width of the head 3, so that the head can be inserted into the receiving part from the bottom end 5b.

The pressure member 6000 has an upper portion with a substantially V-shaped recess 61 for the rod 100 and a lower portion with a head receiving recess 690. The lower portion is substantially cylindrical and may have a slightly reduced outer width compared to the upper portion, so that a step 6c may be formed therebetween. Adjacent to the bottom end 6b, an outer tapered surface portion 680 is formed that is configured to cooperate with the narrowing portion 520 in the receiving part 500. The head receiving recess 690 has a first spherical section 691 adjacent to the lower end 6b that serves as a seat for the head 3 to pivot therein. Further, the head receiving recess 690 has a second portion 692 that may be cylindrical or otherwise shaped and serves for providing space for an upper edge of the head when the head pivots. Finally, a third narrowing section 693 narrows towards a threaded bore 666, which in turn is configured to house the insert member 700 therein. The thread may extend into the narrowing section 693. The threaded bore 666 may extend in the axial direction to a position above the bottom 62 of the V-shaped recess 61.

The head receiving recess 690 is defined by a plurality of flexible wall sections 694 that are separated by slits 695 which open towards the lower end 6b. The slits 695 may extend to the upper head receiving section 692 and may have widened closed ends 695a to generate a certain degree of flexibility for compressing an inserted head 3. A thread of the threaded bore 666 may extend above the bottom of the recess 61 and may end at a small distance below the through-holes 650.

The pressure member 6000 and the insert member 700 may be pre-assembled so that the spherical recess 720 of the insert member faces the direction of the lower end 6b of the pressure member. The pre-assembled pressure member 6000 and insert member 700 are inserted into the receiving part 500 and rotationally aligned by the pins 57 extending into the through-holes 650. The insert member 700 can be positioned to slightly extend above the bottom 62 of the substantially V-shaped recess 61 without being touched by an inserted rod (see, for example, FIG. 33). To prevent removal of the pressure member 6000 through the lower opening 520b when the head 3 is not inserted, the pressure member 6000 may abut against the step 510b in the passage 510 of the receiving part with the step 6c formed between the upper portion and the lower portion of the pressure member. When the lower portion of the pressure member extends into the narrowing portion 520, the head 3 is prevented from being removed through the lower opening.

In a first manner of use, the bone anchoring element 1 is first inserted into bone, and thereafter the receiving part with assembled pressure member 6000 and insert member 700 is mounted onto the head 3. For mounting, the head 3 enters through the lower opening 520b of the receiving part and into the head receiving recess 690, whereby the inner wall sections 694 spread apart and snap over the head 3. In another manner of use, the bone anchoring element 1 is already inserted into the receiving part and the pressure member before the bone anchoring element is implanted into bone.

Figures 42A, 42B:
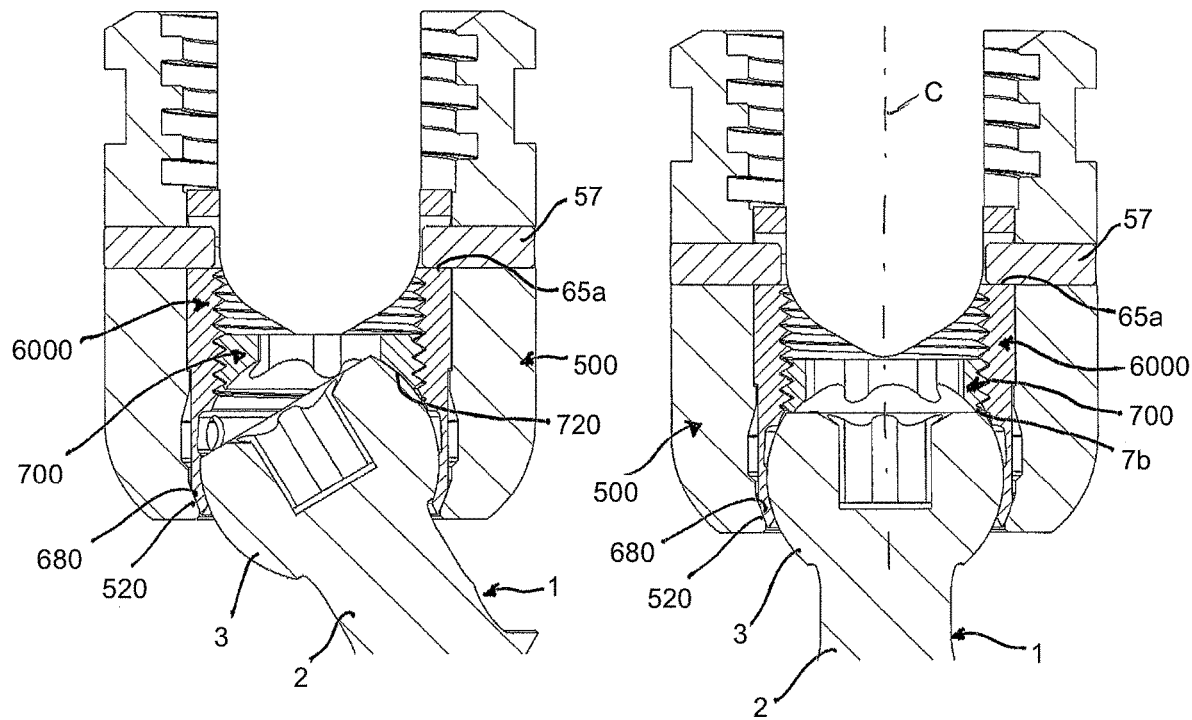
FIGS. 42a and 42b show steps of using the polyaxial bone anchoring device according to the third embodiment.

Turning now to FIGS. 42a and 42b, functions and ways of using the bone anchoring device according to the third embodiment will be described. In the configuration of FIG. 42a, the insert member 700 is at a height such that the head 3 can pivot in the head receiving recess 720. The pressure member 6000 abuts with the lower ends 65a of the through-holes 650 against the pins 57, respectively. Tightening of the insert member 700 generates a frictional force that holds the head 3 by friction but still allows the head 3 to pivot. Further tightening results in a provisional locking of the head 3 without the rod being inserted.

In the configuration of FIG. 42b, the bone anchoring element 1 is in the zero angular position of the shank 2 relative to the central axis C of the receiving part and is held in the zero angular position by screwing the insert member 700 towards the head until the lower end 7b of the insert member 700 abuts onto the free end surface 3a of the head. Thereby the bone anchoring element is held in the zero angular position and works as a monoaxial screw without a rod being inserted.

As in the other embodiments, finally, the rod can be inserted, and with further insertion and advancement of the locking member, a locking force can be provided to the whole construct that may be stronger compared to the provisional locking configuration.

Various modifications of the embodiments described above are also conceivable. The features of one embodiment can be combined with those of other embodiments to provide a variety of further embodiments. The parts are also not limited to their detailed shapes as depicted in the embodiments. While the abutments of the pressure member at the receiving part are shown as pins, other abutments are also conceivable. Also, only one pin may be sufficient. The advancement structure between the pressure member and the insert member can be another structure in other embodiments, or can even be a friction-fit cooperation between the pressure member and the insert member that allows continuous or gradual movement of the insert member relative to the pressure member. Other modifications of the head contacting surface of the insert member may also be conceivable that render the insert member suitable for restricting pivotal motion of the head relative to the insert member. For the locking member, other known locking members may instead be used, for example, a two part locking member that permits locking of the head and the rod separately. The pressure member may have in such embodiments legs that extend above the surface of the rod.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
   a receiving part having a first end, a second end below the first end, a central axis extending between the first and second ends, and a coaxial passage extending therethrough, wherein the receiving part is configured to pivotably receive a head of an anchoring element such that the anchoring element can assume a plurality of angular positions relative to the receiving part;
   a pressure member positionable and movable in the passage; and
   an insert member positionable at least partially in the pressure member and movable axially relative to the pressure member between a first position and a second position for exerting an adjustable pressure on the head of the anchoring element to lock the head relative to the receiving part;
   wherein when the pressure member is in the passage and the insert member is in the pressure member, a first engagement structure of the insert member that has at least one of an upwardly facing engagement surface or a downwardly facing engagement surface is configured to engage a second engagement structure of the pressure member to releasably hold the insert member at the first position against movement towards the second position and to releasably hold the insert member at the second position against movement towards the first position.

2. The bone anchoring device of claim 1, wherein the pressure member defines a central bore and the insert member is movable at least partially in the central bore.

3. The bone anchoring device of claim 1, wherein the first and second engagement structures form an advancement structure between the pressure member and the insert member.

4. The bone anchoring device of claim 3, wherein the advancement structure comprises threads.

5. The bone anchoring device of claim 1, wherein the pressure member is movable axially in the passage, and wherein the receiving part comprises an abutment that restricts upward movement of the pressure member to provide a counterforce when the insert member presses onto an inserted head.

6. The bone anchoring device of claim 1, wherein the pressure member comprises a support surface for a rod, and wherein an opening is provided in the support surface to provide access to the insert member when a rod is not inserted in the receiving part.

7. The bone anchoring device of claim 1, wherein the pressure member further comprises a stop that is different from the second engagement structure for limiting upward movement of the insert member relative to the pressure member.

8. The bone anchoring device of claim 1, further comprising the anchoring element comprising a head and a shank for anchoring in bone.

9. The bone anchoring device of claim 8, wherein the insert member comprises a head contacting surface configured to facilitate pivoting of the head relative to the insert member for the shank to assume a plurality of angular positions relative to the receiving part.

10. The bone anchoring device of claim 9, wherein the insert member exerts a first pressure on the head at the first position to hold the head at an angular position that can be adjusted by overcoming the first pressure, and wherein the insert member exerts a second pressure on the head that is greater than the first pressure at the second position to provisionally lock the angular position of the head.

11. The bone anchoring device of claim 8, wherein the insert member comprises a head contacting surface with a shape configured to provide a connection with the head so that the shank is held at a set angular position relative to the receiving part.

12. The bone anchoring device of claim 11, wherein the set angular position is a zero angle position where the shank is substantially aligned with the central axis.

13. The bone anchoring device of claim 11, wherein the shape of the head contacting surface is configured to provide a form-fit connection with the head.

14. The bone anchoring device of claim 11, wherein the head contacting surface comprises an edge configured to provide feedback when the head is pivoted in and/or out of the set angular position.

15. The bone anchoring device of claim 14, wherein the edge is formed at a lower end of the insert member and is configured to contact a free end surface of the head.

16. The bone anchoring device of claim 8, wherein the pressure member comprises flexible legs configured to be resiliently compressed by a portion of the receiving part to exert a biasing force on the head.

17. The bone anchoring device of claim 8, wherein the anchoring element is insertable from the first end of the receiving part and the pressure member is configured to exert pressure on an upper side of the head.

18. The bone anchoring device of claim 8, wherein the anchoring element is insertable from the second end of the receiving part and the bone anchoring device comprises a compressible portion configured to exert lateral pressure on the head.

19. The bone anchoring device of claim 8, further comprising a locking member configured to act directly or via an inserted rod on the pressure member to lock the head relative to the receiving part.

20. A kit comprising the bone anchoring device of claim 8, wherein the insert member is a first insert member, and further comprising a second insert member interchangeable with the first insert member, wherein the first insert member has a head contacting surface that permits polyaxial movement of the head relative to the receiving part, and the second insert member has a head contacting surface configured to hold the head in a monoaxial position relative to the receiving part.

21. A bone anchoring device comprising:
   a receiving part having a first end, a second end below the first end, a central axis extending between the first and second ends, and a coaxial passage extending therethrough, wherein the receiving part is configured to pivotably receive a head of an anchoring element such that the anchoring element can assume a plurality of angular positions relative to the receiving part;

a pressure member positionable and movable in the passage; and an insert member engageable with and positionable at least partially in the pressure member;

wherein when the pressure member is in the passage, the insert member is in the pressure member, and while the pressure member remains stationary at a same axial position in the receiving part, the insert member is movable axially relative to the receiving part, while a first engagement structure of the insert member that has at least one of an upwardly facing engagement surface or a downwardly facing engagement surface is configured to engage a second engagement structure of the pressure member for releasably holding the insert member at at least three distinct axial positions relative to the receiving part.

22. A method of coupling a rod to a bone using a bone anchoring device comprising an anchoring element comprising a head and a shank for anchoring in bone, a receiving part having a first end, a second end below the first end, a central axis extending between the first and second ends, and a coaxial passage extending therethrough, wherein the receiving part is configured to pivotably receive the head such that the anchoring element can assume a plurality of angular positions relative to the receiving part, a pressure member positionable and movable in the passage, an insert member positionable at least partially in the pressure member and movable axially relative to the pressure member between a first position and a second position for exerting an adjustable pressure on the head of the anchoring element to lock the head relative to the receiving part, wherein a first engagement structure of the insert member that has at least one of an upwardly facing engagement surface or a downwardly facing engagement surface is configured to engage a second engagement structure of the pressure member to releasably hold the insert member at the first position against movement towards the second position and to releasably hold the insert member at the second position against movement towards the first position, and a locking member, the method comprising:

anchoring the shank of the anchoring element in bone;

adjusting the angular position of the receiving part relative to the shank when the head is in the receiving part, the pressure member is in the passage, and the insert member is at the first position in the pressure member;

adjusting the insert member to the second position to lock the angular position of the receiving part relative to the shank;

connecting the rod to the receiving part;

inserting the locking member into the receiving part; and advancing the locking member in the receiving part to lock the rod relative to the receiving part.

* * * * *